(12) United States Patent
Gotou et al.

(10) Patent No.: US 9,709,702 B2
(45) Date of Patent: Jul. 18, 2017

(54) SPECIAL POLYCARBONATE POLARIZING EYEWEAR (71) Applicants: MITSUBISHI GAS CHEMICAL COMPANY, INC., Tokyo (JP); MGC FILSHEET CO., LTD., Saitama (JP)

(72) Inventors: Takuya Gotou, Ibaraki (JP); Kazuhisa Mitsuhata, Tokyo (JP); Kyousuke Nakamura, Chiba (JP); Masatoshi Nakashima, Saitama (JP)

(73) Assignees: MITSUBISHI GAS CHEMICAL COMPANY, INC., Tokyo (JP); MGC FILSHEET CO., LTD., Saitama (JP)

( * ) Notice: Subject to any disclaimer, the term of this patent is extended or adjusted under 35 U.S.C. 154(b) by 339 days.

(21) Appl. No.: 14/420,799

(22) PCT Filed: Aug. 12, 2013

(86) PCT No.: PCT/JP2013/071756
§ 371 (c)(1),
(2) Date: Feb. 10, 2015

(87) PCT Pub. No.: WO2014/027633
PCT Pub. Date: Feb. 20, 2014

(65) Prior Publication Data
US 2015/0205011 A1    Jul. 23, 2015

(30) Foreign Application Priority Data

Aug. 14, 2012   (JP) .................................. 2012-179788

(51) Int. Cl.
C08G 63/00    (2006.01)
C08L 69/00    (2006.01)
(Continued)

(52) U.S. Cl.
CPC .............. *G02B 1/041* (2013.01); *B32B 27/08* (2013.01); *B32B 27/306* (2013.01);
(Continued)

(58) Field of Classification Search
CPC ....... C08G 64/06; B32B 27/08; B32B 27/306; B32B 27/365; B32B 2250/03;
(Continued)

(56) References Cited

U.S. PATENT DOCUMENTS 5,051,309 A    9/1991 Kawaki et al.
5,486,577 A    1/1996 Farah et al.
(Continued)

FOREIGN PATENT DOCUMENTS

CN    1572836       2/2005
EP    1 394 595     3/2004
(Continued)

OTHER PUBLICATIONS

Search report from PCT/JP2013/071756, mail date is Oct. 8, 2013.

*Primary Examiner* — William Cheung
(74) *Attorney, Agent, or Firm* — Greenblum & Bernstein, P.L.C.

(57) ABSTRACT

Eyewear uses a polarizing lens obtained by bending a multilayer polarizing sheet in which a sheet (A) including at least 50% by mass of an aromatic polycarbonate resin and having a retardation value of 2000 nm or less at a wavelength of 600 nm is layered on one side of a polarizing film, and a sheet (B) including a special polycarbonate resin obtained by carbonate bonding a dihydroxy compound through use of a carbonic acid diester, the polycarbonate resin being a compound in which 70-100 mol % of the dihydroxy compound is represented by general formula (1), is layered on the other side of the polarizing film.

(Continued)

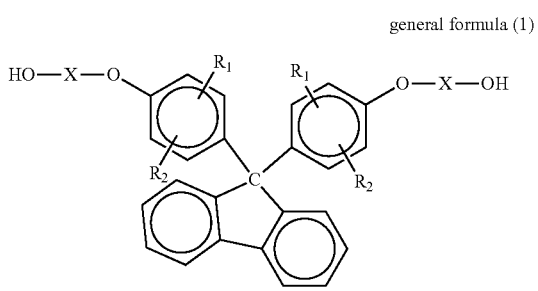

general formula (1)

(In general formula (1), $R_1$ and $R_2$ are each independently a hydrogen atom, a $C_1$-$C_{20}$ alkyl group, or the like. In general formula (1), X are each independently a $C_2$-$C_8$ alkylene group or the like.)

13 Claims, 3 Drawing Sheets (51) Int. Cl.

| | |
|---|---|
| *C08K 3/34* | (2006.01) |
| *D02G 3/00* | (2006.01) |
| *B32B 27/00* | (2006.01) |
| *B32B 9/00* | (2006.01) |
| *C08G 64/00* | (2006.01) |
| *C08G 65/38* | (2006.01) |
| *G02C 7/12* | (2006.01) |
| *G02B 1/04* | (2006.01) |
| *C08G 64/06* | (2006.01) |
| *B32B 27/08* | (2006.01) |
| *B32B 27/30* | (2006.01) |
| *B32B 27/36* | (2006.01) |
| *G02B 5/30* | (2006.01) |
| *A61F 9/02* | (2006.01) |

(52) U.S. Cl.
CPC ............ *B32B 27/365* (2013.01); *C08G 64/06* (2013.01); *G02C 7/12* (2013.01); *A61F 9/022* (2013.01); *B32B 2250/03* (2013.01); *B32B 2307/42* (2013.01); *B32B 2551/00* (2013.01); *G02B 5/305* (2013.01); *G02B 5/3041* (2013.01); *G02C 2202/16* (2013.01)

(58) Field of Classification Search
CPC . B32B 2307/42; B32B 2551/00; G02B 1/041; G02B 5/305; G02B 5/3041; G02C 7/12; G02C 2202/16; A61F 9/022
USPC ........... 351/49; 528/196, 198, 219; 428/401, 428/500, 690; 524/445, 449; 525/437, 525/439
See application file for complete search history.

(56) References Cited

U.S. PATENT DOCUMENTS

| 5,702,813 A | 12/1997 | Murata et al. |
| 2004/0245511 A1 | 12/2004 | Fujimori et al. |
| 2007/0123685 A1* | 5/2007 | Fujimori ............ C08G 64/1608 528/196 |
| 2009/0305049 A1 | 12/2009 | Kobuchi et al. |

FOREIGN PATENT DOCUMENTS

| JP | 3-39903 | 2/1991 |
| JP | 8-52817 | 2/1996 |
| JP | 08-313701 | 11/1996 |
| JP | 2000-169573 | 6/2000 |
| JP | 2001-305341 | 10/2001 |
| JP | 2005-025149 | 1/2005 |
| JP | 2005-031611 | 2/2005 |
| JP | 2008-163194 | 7/2008 |
| JP | 2009-294445 | 12/2009 |
| JP | 2012-103507 | 5/2012 |
| WO | 2011/049108 | 4/2011 |

* cited by examiner

SPECIAL POLYCARBONATE POLARIZING EYEWEAR

RELATED APPLICATIONS

This application is a National Stage Entry of International Application No. PCT/JP2013/071756, filed Aug. 12, 2013, and claims the benefit of and priority to Japan Patent Application No. 2012-179788, filed Aug. 14, 2012, all of which are incorporated herein by reference in their entirety.

TECHNICAL FIELD

The present invention relates to a glare-proof eyewear (sunglasses, goggles, etc.) obtained by subjecting a polycarbonate multilayer polarizing sheet to a curving process to provide a curved surface shape. Further, the present invention includes a glare-proof eyewear formed by subjecting a polycarbonate multilayer polarizing sheet to a curving process to provide a curved surface shape and then injection-molding a polycarbonate on one of the surfaces of the sheet.

BACKGROUND ART

Polarizing sheets made of an aromatic polycarbonate have excellent impact resistance and are light, and therefore are used for liquid crystal displays as well as windows of buildings, sunroofs of cars, etc.

Further, polarizing sheets, which are obtained by laminating an aromatic polycarbonate sheet as a protection layer through an adhesive layer to each surface of a polarizing sheet obtained by stretching a polyvinyl alcohol film and staining it with a dichroism pigment (hereinafter referred to as "aromatic polycarbonate polarizing sheet"), particularly have excellent impact resistance and also have high heat resistance, and therefore are used for polarizing lenses for eyewear (sunglasses, goggles, etc.) to be used for marine sports, winter sports, fishing, etc. obtained from a curving process or injection molding process.

However, since aromatic polycarbonate has a high photoelastic constant, when a curving process is applied to a spherical or aspherical shape of sunglasses, goggles or the like, a coloring interference stripe (iridescent pattern) tends to easily occur due to retardation. Such a coloring interference stripe causes poor outer appearance of a polarizing lens, and this is a major problem particularly in the field of eyewear in which the beauty of outer appearance affects purchasing power for products. Moreover, such a coloring interference stripe also has a problem that health problems such as eye strain are caused thereby.

Regarding handling of retardation caused at the time of applying a curving process, an aromatic polycarbonate polarizing sheet, whose coloring interference stripe has been hidden from view by subjecting an aromatic polycarbonate sheet to be used for a protection layer to a stretching process to cause a large retardation in advance (hereinafter referred to as "stretched polycarbonate polarizing sheet"), is known (Patent Document 1).

However, when using the stretched polycarbonate polarizing sheet, it is possible to prevent occurrence of a coloring interference stripe, but since the aromatic polycarbonate sheet has been stretched, the aromatic polycarbonate is contracted in the stretching direction at the time of the curving process, and the absolute value of the difference between the base curve in the vertical direction and the base curve in the horizontal direction of the formed polarizing lens (hereinafter referred to as "base curve anisotropy") increases, causing the problem of reduction in the resolution of the lens.

Meanwhile, a polarizing lens, which is formed by subjecting the afore-mentioned stretched polycarbonate polarizing sheet to a curving process to provide a spherical or aspherical shape, inserting the resultant stretched polycarbonate polarizing sheet into a mold and injecting an aromatic polycarbonate thereto, for the purpose of improving impact resistance to be more than that of a polarizing lens formed by subjecting the afore-mentioned stretched polycarbonate polarizing sheet to a curving process or forming a corrective lens having a focal refractive power, is known (Patent Documents 2 and 3). However, the problems of occurrence of a coloring interference stripe and the resolution have not been solved even by such a polarizing lens.

Further, a method of using an aromatic polycarbonate sheet in which the stretch thereof has been eliminated or decreased on the concave surface side for the purpose of preventing occurrence of a coloring interference stripe at the time of the curving process and improving the curved shape is also known (Patent Document 3). However, even in this case, a stretched aromatic polycarbonate sheet is used on the convex surface side, and therefore, reduction in the resolution due to the curved shape base curve anisotropy is not improved sufficiently.

It is known that a film comprising a polycarbonate resin, which is obtained by carbonate bonding two types of components that are 99 to 5 mol % of a compound represented by general formula (1) below and 1 to 95 mol % of a dihydroxy compound other than that using a carbonic acid diester, is an optical film having good balance between low birefringence, high transparency and high glass-transition temperature (see Patent Document 4). Further, a polarizing sheet in which such a film is used as a protection film for the polarizing sheet of a flat panel display has been reported (see Patent Document 5), but use of such a polarizing sheet comprising a special polycarbonate resin as a polarizing sheet for a polarizing lens to be subjected to a curving process has not been studied.

general formula (1)

PRIOR ART DOCUMENTS

Patent Documents

Patent Document 1: Japanese Laid-Open Patent Publication No. H03-39903
Patent Document 2: Japanese Laid-Open Patent Publication No. H08-52817
Patent Document 3: Japanese Laid-Open Patent Publication No. H08-313701
Patent Document 4: Japanese Laid-Open Patent Publication No. 2008-163194
Patent Document 5: Japanese Laid-Open Patent Publication No. 2012-103507

SUMMARY OF THE INVENTION

Problems to be Solved by the Invention

The purpose of the present invention is to provide a polycarbonate polarizing eyewear having a high resolution while preventing generation of iridescent patterns during the curving process.

Means for Solving the Problems

The present inventor diligently made researches in order to accomplish the aforementioned purpose, and achieved the present invention by using a multilayer polarizing sheet in which a sheet (A) including at least 50% by mass of an aromatic polycarbonate resin and having a retardation value of 2000 nm or less at a wavelength of 600 nm is layered on one side of a polarizing film, and a polycarbonate sheet (hereinafter referred to as "the sheet (B)" or "the special polycarbonate sheet") including a polycarbonate resin (hereinafter referred to as "the special polycarbonate resin") obtained by carbonate bonding a dihydroxy compound through use of a carbonic acid diester, the polycarbonate resin being a compound in which 70 to 100 mol % of the dihydroxy compound is represented by general formula (1), is layered on the other side of the polarizing film:

general formula (1)

(In general formula (1), $R_1$ and $R_2$ are each independently a hydrogen atom, a $C_1$-$C_{20}$ alkyl group, a $C_1$-$C_{20}$ alkoxyl group, a $C_5$-$C_{20}$ cycloalkyl group, a $C_5$-$C_{20}$ cycloalkoxyl group, a $C_6$-$C_{20}$ aryl group or a $C_6$-$C_{20}$ aryloxy group; and Xs are each independently a $C_2$-$C_8$ alkylene group, a $C_5$-$C_{12}$ cycloalkylene group or a $C_6$-$C_{20}$ arylene group.)

Specifically, the present invention provides a special polycarbonate polarizing eyewear as described below.
1. An eyewear which uses a polarizing lens obtained by bending a multilayer polarizing sheet in which a sheet (A) including at least 50% by mass of an aromatic polycarbonate resin and having a retardation value of 2000 nm or less at a wavelength of 600 nm is layered on one side of a polarizing film, and a sheet (B) including a special polycarbonate resin obtained by carbonate bonding a dihydroxy compound through use of a carbonic acid diester, the polycarbonate resin being a compound in which 70 to 100 mol % of the dihydroxy compound is represented by general formula (1), is layered on the other side of the polarizing film.
2. The eyewear according to item 1, wherein 80 to 95 mol % of the whole dihydroxy compound constituting the resin included in the sheet (B) is a compound represented by general formula (1).
3. The eyewear according to item 1 or 2, wherein: the resin included in the sheet (B) consists of only the special polycarbonate resin; 80 to 95 mol % of the dihydroxy compound constituting the special polycarbonate resin is a compound represented by general formula (1); and the remaining 20 to 5 mol % of the dihydroxy compound is a dihydroxy compound other than the compound represented by general formula (1).
4. The eyewear according to item 1 or 2, wherein: the resin included in the sheet (B) consists of the special polycarbonate resin and an aromatic polycarbonate resin; 100 mol % of the dihydroxy compound constituting the special polycarbonate resin is a compound represented by general formula (1); the dihydroxy compound constituting the aromatic polycarbonate resin is a dihydroxy compound other than the compound represented by general formula (1); and 80 to 95 mol % of the whole dihydroxy compound constituting the resin included in the sheet (B) is the compound represented by general formula (1).
5. The eyewear according to any one of items 1 to 4, wherein the temperature difference between the glass-transition temperature of the sheet (B) and the glass-transition temperature of the aromatic polycarbonate resin having a retardation value of 2000 nm or less is 10° C. or less.
6. The eyewear according to any one of items 1 to 5, wherein in the compound represented by general formula (1), $R_1$ and $R_2$ are a hydrogen atom and Xs are an ethylene group.
7. The eyewear according to any one of items 1 to 6, wherein the dihydroxy compound other than the compound represented by general formula (1) is a compound represented by the below-described structural formula (1):

structural formula (1)

8. The eyewear according to any one of items 1 to 6, wherein the dihydroxy compound other than the compound represented by general formula (1) is a compound represented by the below-described general formula (2):

general formula (2)

wherein in general formula (2), Y is a $C_1$-$C_{10}$ alkylene group or a $C_4$-$C_{20}$ cycloalkylene group.
9. The eyewear according to item 8, wherein the compound represented by general formula (2) is at least one selected from tricyclo[5.2.1.0$^{2,6}$]decanedimethanol, cyclohexane-1,4-dimethanol and pentacyclopentadecanedimethanol.
10. The eyewear according to item 8, wherein the compound represented by general formula (2) is tricyclo[5.2.1.0$^{2,6}$]decanedimethanol.
11. The eyewear according to any one of items 1 to 10, wherein the retardation value of the sheet (B) at a wavelength of 600 nm is 20 nm or less.
12. The eyewear according to any one of items 1 to 11, which is subjected to a curving process to have a spherical or non-spherical surface so that the surface at the sheet (B) side becomes a convex surface.
13. The eyewear according to item 12, wherein an aromatic polycarbonate resin is further injection-molded on the concave surface.

Advantageous Effect of the Invention

According to the present invention, it is possible to provide a multilayer polarizing lens having a high resolution while preventing generation of iridescent patterns during the curving process. Further, in the case of a multilayer polarizing lens having the aforementioned constitution, a desired curved shape can be easily obtained while preventing generation of iridescent patterns during the curving process, and therefore, it can realize polarizing eyewear having unprecedented characteristics with excellent aesthetics while ensuring functions which are equal to or more than those of conventional polarizing eyewear.

EMBODIMENTS FOR CARRYING OUT THE INVENTION

Hereinafter, the multilayer polarizing lens of the present invention will be described.
For obtaining the multilayer polarizing sheet of the present invention, firstly, a polarizing film is prepared, and a sheet (B) including a special polycarbonate resin is layered on one side of the polarizing film. Next, a sheet (A) including at least 50% by mass of an aromatic polycarbonate resin and having a retardation value of 2000 nm or less at a wavelength of 600 nm is layered to provide a multilayer polarizing sheet. In the multilayer polarizing sheet thus prepared, between the polarizing film and the aromatic polycarbonate resin, another resin sheet (e.g., a special polycarbonate sheet) may exist. Next, the above-described multilayer polarizing sheet is subjected to the curving process to provide a multilayer polarizing lens for eyewear. When further forming a corrective lens having impact resistance and focus refracting force, polycarbonate may be further injection-molded on the curved multilayer polarizing sheet.
Hereinafter, respective layers constituting the multilayer polarizing lens of the present invention will be described.
Polarizing Film
The method for preparing the polarizing film is not particularly limited, but for example, a resin film as a base material is swollen in water, and then immersed in a staining solution containing a dye such as a dichroism pigment while being directionally stretched to disperse the dichroism pigment in the base resin in an oriented state, thereby obtaining a polarizing film to which polarization properties have been imparted.
Aromatic Polycarbonate Sheet (Sheet (A))
The method for laminating a protection layer consisting of the aromatic polycarbonate sheet is not particularly limited, but examples thereof include a method in which the protection layer is laminated to one surface of the polarizing film through an adhesive layer.

The aromatic polycarbonate resin of the present invention is a resin totally different from the special polycarbonate resin and includes a dihydroxy compound other than the compound represented by the above-described general formula (1) as a constituent thereof, and it is a thermoplastic polycarbonate polymer that may be branched, which is produced by reacting an aromatic dihydroxy compound or it and a small amount of a polyhydroxy compound with phosgene or carbonic acid diester. The aforementioned aromatic polycarbonate resin may be included in the aromatic polycarbonate sheet in an amount of at least 50% by mass, preferably at least 80% by mass, and more preferably at least 90% by mass. Other components may be added thereto, but most preferably, 100% by mass of the aromatic polycarbonate resin is included in the aromatic polycarbonate sheet. The aromatic dihydroxy compound to be used in the present invention is a compound represented by general formula (A) or general formula (B) below.

general formula (A)

general formula (B)

In the general formula (A) above,

In this regard, $R_3$ and $R_4$ are a hydrogen atom or a $C_1$-$C_{10}$ alkyl group or halogen, and $R_3$ and $R_4$ may be the same or different. Further, m and n represent the number of substituents and are an integer from 0 to 4. $R_5$ and $R_6$ are a hydrogen atom or a $C_1$-$C_{10}$ alkyl group or a phenyl group, and $R_5$ and $R_6$ may be bonded to each other to form a ring.
Examples of the aromatic dihydroxy compound represented by general formula (A) or general formula (B) above to be used include bis(4-hydroxyphenyl)methane, 1,1-bis(4-hydroxyphenyl)ethane, 2,2-bis(4-hydroxyphenyl)propane, 2,2-bis(4-hydroxyphenyl)butane, 2,2-bis(4-hydroxyphenyl)octane, bis(4-hydroxyphenyl)phenylmethane, 2,2-bis(4-hydroxy-3-methylphenyl)propane, 1,1-bis(4-hydroxy-3-tert-butylphenyl)propane, 2,2-bis(4-hydroxy-3-bromophenyl)propane, 1,1-bis(4-hydroxyphenyl)cyclopentane, 1,1-bis(4-hydroxyphenyl)cyclohexane, 4,4'-dihydroxydiphenylether, 4,4'-dihydroxy-3,3'-dimethylphenylether, 4,4'-dihydroxyphenylsulfide, 4,4'-dihydroxy-3,3'-dimethyldiphenylsulfide, 4,4'-dihydroxydiphenylsulfoxide, 4,4'-dihydroxy-3,3'-dimethyldiphenylsulfoxide, 4,4'-dihydroxydiphenylsulfone, 4,4'-dihydroxydiphenylsulfone and 4,4'-dihydroxy-3,3'-dimethyldiphenylsulfone. Among them, 2,2'-bis(4-hydroxyphenyl)propane (bisphenol A: BPA) is particularly preferred. Further, 2 or more types of the aromatic dihydroxy compounds represented by general formula (A) can be used in combination.

The glass-transition temperature of such aromatic polycarbonate is about 135 to 155° C.

<Other Components>

The aforementioned other components are not particularly limited and can be suitably selected depending on purposes. Examples thereof include an antioxidant, a mold release agent, an ultraviolet absorber, a flowability improving agent, a crystal nucleating agent, a toughening agent, a dye, an antistatic agent and an antimicrobial agent. These components may be used solely, or two or more of them may be used in combination.

Regarding the molecular weight of the aromatic polycarbonate sheet, the viscosity-average molecular weight is preferably 12,000 to 40,000 from the viewpoint of the formation of the sheet itself, and particularly preferably 20,000 to 35,000 from the viewpoint of the strength, heat resistance, durability or curving workability of the sheet.

The retardation value of the aromatic polycarbonate sheet at a wavelength of 600 nm may be 2000 nm or less from the viewpoint of the improvement of precision of the surface shape during the curving process, and is desirably 1000 nm or less, and particularly desirably 500 nm or less. The lowest value of the retardation value is 0 nm that is the limit that can be measured.

Special Polycarbonate Sheet (Sheet (B))

The special polycarbonate resin included in the special polycarbonate sheet to be used in the present invention includes at least a predetermined special polycarbonate resin, and may further include other components according to need. The method for laminating a protection layer consisting of the special polycarbonate sheet is not particularly limited, but examples thereof include a method in which the protection layer is laminated to one surface of the polarizing film through an adhesive layer.

Regarding the special polycarbonate resin constituting the special polycarbonate sheet described above, it is sufficient when it is a resin, which is obtained by reacting the dihydroxy compound including the compound represented by general formula (1) as an essential component with phosgene or carbonic acid diester, wherein 70 to 100 mol % of the dihydroxy compound is the compound represented by general formula (1), and there is no particular limitation thereon. The resin can be suitably selected depending on purposes. It is sufficient when the concentration of the special polycarbonate resin in the special polycarbonate sheet is at least 50% by mass, and the concentration is preferably at least 80% by mass, and more preferably at least 90% by mass.

general formula (1)

(In general formula (1), $R_1$ and $R_2$ are each independently a hydrogen atom, a $C_1$-$C_{20}$ alkyl group, a $C_1$-$C_{20}$ alkoxyl group, a $C_5$-$C_{20}$ cycloalkyl group, a $C_5$-$C_{20}$ cycloalkoxyl group, a $C_6$-$C_{20}$ aryl group or a $C_6$-$C_{20}$ aryloxy group. Further, in general formula (1), Xs are each independently a $C_2$-$C_8$ alkylene group, a $C_5$-$C_{12}$ cycloalkylene group or a $C_6$-$C_{20}$ arylene group.)

In a preferred embodiment of the present invention, 80 to 95 mol % of the whole dihydroxy compound constituting the resin included in the special polycarbonate sheet is the compound represented by the general formula (1). In this regard, the resin included in the special polycarbonate sheet includes not only the special polycarbonate resin, but also an aromatic polycarbonate resin other than that, etc. Further, the aforementioned whole dihydroxy compound means the total amount of the dihydroxy compound, which includes not only the compound represented by the general formula (1), but also a dihydroxy compound other than that. In a more preferred embodiment, 85 to 90 mol % of the whole dihydroxy compound constituting the resin included in the special polycarbonate sheet is the compound represented by the general formula (1), and in a particularly preferred embodiment, 87 mol % of the whole dihydroxy compound constituting the resin included in the special polycarbonate sheet is the compound represented by the general formula (1).

In another preferred embodiment of the present invention, the resin included in the special polycarbonate sheet consists of only the special polycarbonate resin (that is, the concentration of the special polycarbonate resin in the special polycarbonate sheet is 100% by mass); 80 to 95 mol % of the dihydroxy compound constituting the special polycarbonate resin is a compound represented by general formula (1); and the remaining 20 to 5 mol % of the dihydroxy compound is a dihydroxy compound other than the compound represented by general formula (1). In a more preferred embodiment, the resin included in the special polycarbonate sheet consists of only the special polycarbonate resin; 85 to 90 mol % of the dihydroxy compound constituting the special polycarbonate resin is the compound represented by general formula (1); and the remaining 15 to 10 mol % of the dihydroxy compound is a dihydroxy compound other than the compound represented by general formula (1). In a particularly preferred embodiment, 87 mol % of the dihydroxy compound constituting the special polycarbonate resin is the compound represented by general formula (1); and the remaining 13 mol % of the dihydroxy compound is a dihydroxy compound other than the compound represented by general formula (1).

In yet another preferred embodiment of the present invention, the resin included in the special polycarbonate sheet consists of the special polycarbonate resin and an aromatic polycarbonate resin; 100 mol % of the dihydroxy compound constituting the special polycarbonate resin is a compound represented by general formula (1); the dihydroxy compound constituting the aromatic polycarbonate resin is a dihydroxy compound other than the compound represented by general formula (1); and 80 to 95 mol % of the whole dihydroxy compound constituting the resin included in the sheet (B) is the compound represented by general formula (1). In a more preferred embodiment, the resin included in the special polycarbonate sheet consists of the special polycarbonate resin and the aromatic polycarbonate resin; 100 mol % of the dihydroxy compound constituting the special polycarbonate resin is the compound represented by general formula (1); the dihydroxy compound constituting the aromatic polycarbonate resin is a dihydroxy compound other than the compound represented by general formula (1); and 85 to 90 mol % of the whole dihydroxy compound constituting the resin included in the sheet (B) is the compound represented by general formula (1). In a particularly preferred embodiment, the resin included in the special polycarbonate sheet consists of the special polycarbonate resin and the aromatic polycarbonate resin; 100 mol % of the dihydroxy compound constituting the special polycarbonate resin is the compound represented by general formula (1); the dihydroxy compound constituting the aromatic polycarbonate resin is a dihydroxy compound other than the compound represented by general formula (1); and 87 mol % of the whole dihydroxy compound constituting the resin included in the sheet (B) is the compound represented by general formula (1).

Compound Represented by General Formula (1)

The compound represented by general formula (1) is not particularly limited and can be suitably selected depending on purposes. Examples thereof include 9,9-bis(4-(2-hydroxyethoxyl)phenyl)fluorene (in the compound represented by general formula (1), $R_1$ and $R_2$ are a hydrogen atom and Xs are an ethylene group), 9,9-bis(4-(2-hydroxyethoxy)-3-methylphenyl)fluorene, 9,9-bis(4-(2-hydroxyethoxy)-3,5-dimethylphenyl)fluorene, 9,9-bis(4-(2-hydroxyethoxy)-3-tert-butylphenyl)fluorene, 9,9-bis(4-(2-hydroxyethoxy)-3-isopropylphenyl)fluorene and 9,9-bis(4-(2-hydroxyethoxy)-3-cyclohexylphenyl)fluorene. These compounds may be used solely, or two or more of them may be used in combination.

Among them, 9,9-bis(4-(2-hydroxyethoxyl)phenyl)fluorene (in the aforementioned general formula (1), $R_1$ and $R_2$ are a hydrogen atom and Xs are an ethylene group) is desirable because it is easier to obtain a desired curved shape since physical properties other than the glass-transition temperature (e.g., moisture vapor transmission rate) can be set to be similar to those of the aromatic polycarbonate resin.

Dihydroxy Compound

The dihydroxy compound other than the compound represented by general formula (1) is not particularly limited and can be suitably selected depending on purposes. Examples thereof include a compound represented by structural formula (1) (bisphenol A) and a compound represented by general formula (2). Examples of the compound represented by general formula (2) include tricyclo[$5.2.1.0^{2,6}$] decanedimethanol, cyclohexane-1,4-dimethanol, decalin-2,6-dimethanol, norbornane dimethanol, pentacyclopentadecanedimethanol, cyclopentane-1,3-dimethanol, 1,4-butanediol and 1,6-hexanediol. As the aforementioned dihydroxy compound, one compound may be selected from the group consisting of the above-described bisphenol A and the compound of general formula (2) and used solely, or two or more compounds may be selected from the group and used in combination.

structural formula (1)

general formula (2)

(In general formula (2), Y is a $C_1$-$C_{10}$ alkylene group or a $C_4$-$C_{20}$ cycloalkylene group.)

As the aforementioned dihydroxy compound other than the compound represented by general formula (1), among the aforementioned compounds, bisphenol A, tricyclo [$5.2.1.0^{2,6}$]decanedimethanol, cyclohexane-1,4-dimethanol and pentacyclopentadecanedimethanol are preferred, and bisphenol A and tricyclo[$5.2.1.0^{2,6}$]decanedimethanol are more preferred, and bisphenol A is particularly preferred.

Carbonic Acid Diester

The aforementioned carbonic acid diester is not particularly limited and can be suitably selected depending on purposes. Examples thereof include diphenyl carbonate, ditolyl carbonate, bis(chlorophenyl)carbonate, m-cresyl carbonate, dimethyl carbonate, diethyl carbonate, dibutyl carbonate and dicyclohexyl carbonate. These substances may be used solely, or two or more of them may be used in combination.

Among them, diphenyl carbonate is preferred because it is easily obtained.

The retardation value of the special polycarbonate sheet of the present invention is desirably 10 nm or less in the whole visible light region.

Further, the retardation value of the special polycarbonate sheet of the present invention at a wavelength of 600 nm is preferably 20 nm or less, and more preferably 10 nm or less. When the retardation value exceeds 20 nm, a coloring interference stripe may be generated in a curved multilayer polarizing lens due to the retardation value. When the retardation value is much longer than visible wavelengths, generation of a coloring interference stripe is reduced.

The photoelastic coefficient of the special polycarbonate sheet of the present invention is preferably $50 \times 10^{-12}$ $m^2/N$ or less, and more preferably $40 \times 10^{-12}$ $m^2/N$ or less. When the photoelastic coefficient exceeds $50 \times 10^{-12}$ $m^2/N$, the retardation value may be increased. When the photoelastic coefficient is within a more preferred range, the retardation value can be decreased, and therefore it is advantageous. The photoelastic coefficient can be measured, for example, by irradiating a cast film having a thickness of 100 μm with a laser light having a wavelength of 633 nm using an ellipsometer (trade name: M220, JASCO Corporation) and measuring change of birefringence relative to change of the load on the film for calculation.

The polystyrene equivalent weight-average molecular weight (Mw) of the aforementioned special polycarbonate resin is not particularly limited and can be suitably selected depending on purposes, but is preferably 20,000 to 300,000, and more preferably 35,000 to 120,000. When the polystyrene equivalent weight-average molecular weight (Mw) of the aforementioned special polycarbonate resin is less than 20,000, the sheet may become fragile. When the polystyrene equivalent weight-average molecular weight exceeds 300,000, the melt viscosity is increased, and it leads to difficulty in removal of resin after the production. In addition, problems such as reduction in the solubility in a solvent, which leads to difficulty in forming a sheet by a cast method, and difficulty in extrusion molding due to increase of the melt viscosity may be caused. The aforementioned polystyrene equivalent weight-average molecular weight can be calculated from the GPC retention time based on the calibration curve produced using a standard polystyrene having an already-known molecular weight (molecular weight distribution=1), using GPC (trade name: GPC System-21H, Showa Denko K.K.) and chloroform as a developing solvent.

The structure of the special polycarbonate resin is not particularly limited and can be suitably selected depending on purposes, and examples thereof include a random structure, a block structure and an alternating copolymer structure.

The temperature difference between the glass-transition temperature of the special polycarbonate sheet and the glass-transition temperature of the aromatic polycarbonate resin having a retardation value of 2000 nm or less is preferably 10° C. or less, and more preferably 5° C. or less. When the temperature difference between the glass-transition temperatures is more than 10° C., the base curve anisotropy increases when performing the curving process, and problems such as reduction in the resolution may be caused. Further, the above-described temperature difference between the glass-transition temperatures can be adjusted by the content of the compound represented by general formula (1) included in the special polycarbonate resin. Specifically, the temperature difference can be adjusted to 10° C. or less by adjusting the content of the compound represented by general formula (1) to 70 mol % or more, and the temperature difference can be adjusted to 5° C. or less by adjusting the content of the compound represented by general formula (1) to 80 mol % or more.

The glass-transition temperature of the special polycarbonate sheet is preferably 135 to 155° C., and more preferably 140 to 150° C.

Note that the glass-transition temperature (Tg) as used herein is in compliance with JIS-K7121 and defined as a middle point glass-transition temperature obtained by the measurement with a differential scanning calorimetry (DSC) (Seiko Instruments Inc.). When a plurality of glass-transition temperatures derived from a plurality of components are confirmed by the DSC measurement, a value calculated from $1/\Sigma(W_n/T_{gn})$ [in the formula, $W_n$ is a mass fraction of each component and $\Sigma W_n=1$, $T_{gn}$ (° C.) is a glass-transition temperature of each component, and n is the type of each component] is defined as the glass-transition temperature. Conditions for the DSC measurement are: about 10 mg of a sample; under nitrogen atmosphere; and a rate of temperature increase of 20° C./min.

Method for Producing the Special Polycarbonate Resin

The method for producing the special polycarbonate resin is not particularly limited and can be suitably selected depending on purposes as long as the resin is produced by carbonate bonding using the carbonic acid diester. For example, the resin can be produced by the methods disclosed in Japanese Patent No. 4196326 and International Publication WO2007/142149 pamphlet.

The feed amount of the compound represented by general formula (1) in the production of the special polycarbonate resin is not particularly limited and can be suitably selected depending on purposes as long as it is 70 to 100 mol % relative to the total of the compound represented by general formula (1) and the dihydroxy compound other than the compound represented by general formula (1), but the feed amount is more preferably 80 to 100 mol %, and particularly preferably 85 to 100 mol %.

When the feed amount of the compound represented by general formula (1) is less than 70 mol %, the birefringence of the special polycarbonate resin increases. When the feed amount of the compound represented by general formula (1) is within the aforementioned preferred range, the birefringence of the special polycarbonate resin decreases, and it is advantageous.

The feed amount of the dihydroxy compound other than the compound represented by general formula (1) in the production of the special polycarbonate resin is not particularly limited and can be suitably selected depending on purposes as long as it is 0 to 30 mol % relative to the total of the compound represented by general formula (1) and the dihydroxy compound other than the compound represented by general formula (1), but the feed amount is more preferably 0 to 20 mol %, and particularly preferably 0 to 15 mol %. When the feed amount of the dihydroxy compound other than the compound represented by general formula (1) exceeds 30 mol %, the birefringence of the special polycarbonate resin increases. When the feed amount of the dihydroxy compound other than the compound represented by general formula (1) is within the aforementioned preferred range, the birefringence of the special polycarbonate resin decreases, and it is advantageous.

The feed amount of the carbonic acid diester in the production of the special polycarbonate resin is not particularly limited and can be suitably selected depending on purposes, but it is preferably 0.97 to 1.20 mol, and more preferably 0.98 to 1.10 mol relative to the total (1 mol) of the compound represented by general formula (1) and the dihydroxy compound other than the compound represented by general formula (1). When the feed amount of the carbonic acid diester is less than 0.97 mol or exceeds 1.20 mol, it may be impossible to obtain a resin having a high molecular weight.

<Other Components>

The aforementioned other components are not particularly limited and can be suitably selected depending on purposes. Examples thereof include an antioxidant, a mold release agent, an ultraviolet absorber, a flowability improving agent, a crystal nucleating agent, a toughening agent, a dye, an antistatic agent and an antimicrobial agent. These components may be used solely, or two or more of them may be used in combination.

The thickness of the special polycarbonate sheet of the present invention is not particularly limited and can be suitably selected depending on purposes, but is preferably 50 to 500 μm, and more preferably 100 to 300 μm. When the thickness is less than 50 μm, the strength may be reduced, and when the thickness exceeds 500 μm, the transparency is reduced, the retardation value increases, and the outer appearance may become poor. When the thickness is within a more preferred range, good outer appearance is obtained while maintaining the strength, and it is advantageous. The thickness can be measured, for example, by using an electronic micro-film thickness meter (trade name: KL1300B, Anritsu Corporation).

The tensile strength of the special polycarbonate sheet of the present invention is not particularly limited and can be suitably selected depending on purposes, but is preferably 60 MPa or more, and more preferably 70 MPa or more. When the tensile strength is less than 60 MPa, the strength may become insufficient. The tensile strength can be measured, for example, by using a tensile strength tester (trade name: Autograph AGS-100G, Shimadzu Corporation) based on ASTM D882-61T.

The method for forming the special polycarbonate sheet of the present invention is not particularly limited and can be suitably selected depending on purposes, and examples thereof include a melt extrusion method and a cast method. Among them, a melt extrusion method is preferred from the viewpoint of the productivity.

Conditions for the melt extrusion method are not particularly limited, and a method using a T-die, an inflation method or the like can be suitably selected depending on purposes, but it is preferred to employ a method using a T-die, which facilitates a process to provide a thickness of 15 to 500 μm with small thickness unevenness.

When using the special polycarbonate sheet so as to be arranged at the light incidence side of the polarizing film, i.e., the opposite side of the human eye during use of eyewear, a coloring interference stripe is not easily generated.

As an adhesive to be used for lamination of the protection layer on the surfaces of the polarizing film, an acrylic resin-based material, a urethane resin-based material, a polyester resin-based material, a melamine resin-based material, an epoxy resin-based material, a silicone-based material or the like may be used, and in particular, from the viewpoint of the adhesive layer itself or transparency and adhesion properties with respect to aromatic polycarbonate resin at the time of adhering, a two-component thermosetting urethane resin consisting of polyurethane prepolymer that is a urethane resin-based material and a curing agent is preferred. The special polycarbonate polarizing sheet is obtained in this way.

As an adhesive for adhesion between the polarizing film and the aromatic polycarbonate sheet (sheet (A)) of the protection layer or the special polycarbonate sheet (sheet (B)), an adhesive in which a photochromic dye is dissolved may be used. Such a multilayer polarizing sheet prepared using a photochromic dye becomes a multilayer polarizing sheet also having the photochromic function, and since the effect of suppressing generation of iridescent patterns is exerted, excellent outer appearance is obtained.

Next, the multilayer polarizing sheet is subjected to the curving process. The method for the curving process is not particularly limited, and the process may be carried out through a step capable of imparting a spherical or aspherical shape depending on purposes. Conditions for the curving process of the multilayer polarizing sheet are not particularly limited, but the sheet must be curved so that it fits the surface of a mold to be used for injection molding. Further, in the case of the polarizing film, a crack in the stretching direction, so-called film cutting tends to be easily generated in the curving process. In view of these points, the mold temperature in the curving process of the multilayer polarizing sheet is preferably a temperature around the glass-transition temperature of the aromatic polycarbonate resin used for the multilayer polarizing sheet. In addition, the temperature of the multilayer polarizing sheet immediately prior to the curving process is preferably adjusted to a temperature which is equal to or higher than a temperature 50° C. lower than the glass-transition temperature of the aromatic polycarbonate resin and lower than the glass-transition temperature by means of the preheating treatment, and particularly preferably adjusted to a temperature which is equal to or higher than a temperature 40° C. lower than the glass-transition temperature and lower than a temperature 5° C. lower than the glass-transition temperature.

Injection-Molded Polycarbonate

In another embodiment of the present invention, an aromatic polycarbonate resin is injected to the multilayer polarizing sheet. Note that when the aromatic polycarbonate resin is injected after the curving process to form a multilayer polarizing lens, for preventing deterioration of the outer appearance due to the refractive index difference, the surface that contacts with the injected aromatic polycarbonate resin is desirably the aromatic polycarbonate resin of the sheet (A). Conditions for injection molding are not particularly limited, but excellent outer appearance is required. From this viewpoint, the mold temperature is preferably a temperature which is equal to or higher than a temperature 50° C. lower than the glass-transition temperature of the aromatic polycarbonate resin used for the multilayer polarizing sheet and lower than the glass-transition temperature, and particularly preferably a temperature which is equal to or higher than a temperature 40° C. lower than the glass-transition temperature and lower than a temperature 15° C. lower than the glass-transition temperature.

Regarding the type of the aromatic polycarbonate resin for injection molding, from the viewpoint of the strength, heat resistance and durability, examples thereof include polymers produced according to a well-known method from a bisphenol compound typified by 2,2-bis(4-hydroxyphenyl)alkane and 2,2-(4-hydroxy-3,5-dihalogenophenyl)alkane. Among them, an aromatic polycarbonate resin derived from 2,2-bis(4-hydroxyphenyl)propane is preferred.

In the case of the injection-molded polycarbonate multilayer polarizing lens, an aromatic polycarbonate resin is injected and filled in a mold, and therefore, there is an advantage that unevenness of the thickness of the inserted multilayer polarizing sheet becomes invisible. Therefore, the lens is used for lens products without focal refractive power which are particularly excellent in impact resistance, outer appearance and prevention of eye strain.

In the case of a lens obtained by filling a mold with a thermosetting resin or thermoplastic resin as in the case of the injection-molded polycarbonate multilayer polarizing lens, the shape of each surface and the thickness of the formed lens can be freely set by suitably setting each surface shape of molds for the lens surfaces and the distance between the surfaces. Therefore, the surface shapes of molds and the distance between the surfaces are set based on the optical design so that the focal refractive power, prism diopter and image distortion of the formed lens become desired values.

In many cases, the surface shape of the formed lens is the same as the surface shape of the mold contacted at the time of forming, but when the surface shape of the lens requires very high precision, in order to compensate decrease of the lens thickness and change of the surface shape due to volume contraction at the time of solidification of the thermosetting resin or thermoplastic resin filled in the mold, the surface shapes of molds for both the surfaces and the distance between the surfaces may be suitably and finely adjusted.

Hard Coating Treatment

Materials of hard coating and processing conditions are not particularly limited, but excellent outer appearance and adhesiveness with respect to the special polycarbonate sheet as the base or inorganic layers such as a mirror coat and an antireflection coat to be subsequently coated are required. From this viewpoint, the burning temperature is preferably a temperature which is equal to or higher than a temperature 50° C. lower than the glass-transition temperature of the aromatic polycarbonate resin used for the multilayer polarizing sheet and lower than the glass-transition temperature, and particularly preferably a temperature which is equal to or higher than a temperature 40° C. lower than the glass-transition temperature and lower than a temperature 15° C. lower than the glass-transition temperature, i.e., a temperature around 120° C. The time required for burning the hard coat is about 30 minutes to 2 hours.

On the surface of the multilayer polarizing lens formed in this way, a hard coating, an antireflection film and the like are suitably formed, and then the lens is fixed to a frame by edging, hole making, screw tightening, etc., thereby providing eyewear (sunglasses, goggles or the like).

EXAMPLES

Hereinafter, the present invention will be specifically described by way of illustrative examples, but the present invention is not limited thereto. Note that Torr as used in the working examples below is a unit of pressure, and 760 Torr corresponds to 1 atm (1 atmospheric pressure).

(Preparation of Special Polycarbonate Sheet A1)

15.46 kg (35.26 mol) of 9,9-bis(4-(2-hydroxyethoxy) phenyl)fluorene, 1.203 kg (5.269 mol) of bisphenol A, 11.269 kg (52.66 mol) of diphenyl carbonate and 0.02602 g ($3.097 \times 10^{-4}$ mol) of sodium hydrogen carbonate were put into a 50 L reactor equipped with a stirring machine and a distillation apparatus, and the mixture was heated to 215° C. under nitrogen atmosphere of 760 Torr (1 atm) over 1 hour and stirred.

After that, the degree of pressure reduction was adjusted to 150 Torr over 15 minutes, and the mixture was held at 215° C. under 150 Torr for 20 minutes and a transesterification reaction was performed. Further, the temperature was increased to 240° C. at a rate of 37.5° C./hr, and the mixture was held at 240° C. under 150 Torr for 10 minutes. After that, the degree of pressure reduction was adjusted to 120 Torr over 10 minutes, and the mixture was held at 240° C. under 120 Torr for 70 minutes. After that, the degree of pressure reduction was adjusted to 100 Torr over 10 minutes, and the mixture was held at 240° C. under 100 Torr for 10 minutes. Further, the degree of pressure reduction was adjusted to 1 Torr or less over 40 minutes, and a polymerization reaction was performed with stirring at 240° C. under 1 Torr or less for 10 minutes. After the reaction was completed, nitrogen was blown into the reactor for pressurization, and a polycarbonate resin produced was taken out while being pelletized. Regarding the obtained polycarbonate resin, Mw=56900 and Tg=145° C. 10.0 kg of this polycarbonate resin was vacuum-dried at 100° C. for 24 hours, and to the resin, 1000 ppm of a high-molecular-weight antioxidant (trade name: IRGANOX1010, BASF Japan Ltd.) was added and 500 ppm of a phosphorus-based antioxidant (ADK STAB PEP-36, ADEKA Co., Ltd.) was added, and the mixture was kneaded at 250° C. using an extruder and pelletized, thereby obtaining a pellet. The molecular weight (Mw) of the pellet was 56100.

The pellet was vacuum-dried at 100° C. for 24 hours, and then a film was formed at a cylinder temperature of 250° C., a die temperature of 250° C. and a roll temperature of 135° C., thereby obtaining a special polycarbonate sheet A1 having a thickness of 300 μm. Regarding the obtained special polycarbonate sheet A1, the photoelastic coefficient was $37 \times 10^{-12}$ m$^2$/N, the retardation value (Re) at a wavelength of 600 nm was 3.6 nm, and the moisture vapor transmission rate was 17 g/m$^2$/day.

Note that the molecular weight (Mw), the glass-transition temperature (Tg), the thickness, the photoelastic coefficient, the retardation value at a wavelength of 600 nm and the moisture vapor transmission rate were measured in manners described below, and the same manners were employed in the below-described working examples and comparative examples.

<Method for Measuring the Molecular Weight (Mw)>

The aforementioned molecular weight (Mw) was calculated from the GPC retention time based on the calibration curve produced using a standard polystyrene having an already-known molecular weight (molecular weight distribution=1), using GPC (trade name: GPC System-21H, Showa Denko K.K.) and chloroform as a developing solvent.

<Method for Measuring the Glass-Transition Temperature (Tg)>

The aforementioned glass-transition temperature (Tg) was measured using a differential scanning calorimetry (DSC) (Seiko Instruments Inc.).

<Method for Measuring the Thickness>

The aforementioned thickness was measured using a dial thickness gauge (trade name: Dial swift gauge Q-1, Ozaki Mfg Co., Ltd.).

<Method for Measuring the Photoelastic Coefficient>

The aforementioned photoelastic coefficient was measured by irradiating a cast film having a thickness of 100 μm with a laser light having a wavelength of 633 nm using an ellipsometer (trade name: M220, JASCO Corporation) and measuring change of birefringence relative to change of the load on the film for calculation.

<Method for Measuring the Retardation Value (Re) at a Wavelength of 600 nm>

The aforementioned retardation value at a wavelength of 600 nm (definition: birefringence Δn×thickness d) was measured by setting and scanning a sheet or film to be measured using an ellipsometer (trade name: M220, JASCO Corporation).

<Method for Measuring the Moisture Vapor Transmission Rate>

The aforementioned moisture vapor transmission rate was measured using L80-4000L (LYSSY AG ZLLIKON) under the condition of 40° C./90% RH in compliance with JIS-K7209 Method A.

<Method for Measuring the Resolution>

Figure 4:
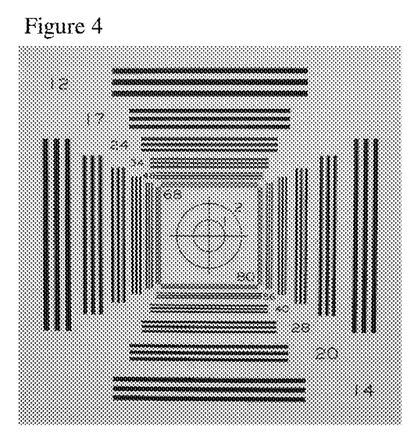
FIG. 4 shows a resolution chart.

The resolution was measured according to the method described in "14.10 Refractive Power, Resolving Power and Astigmatism Tests" in the American Standard ANSI-Z87.1. As the resolution chart, the chart of FIG. 4 was used.

<Method for Observing Iridescent Patterns>

Method for measuring optical distortion: Each lens obtained as described above was measured according to the below-described method. A commercially-available fluorescent desk lamp (neutral white, 15-watt bulb) was covered with a polarizing plate having a polarization degree of 99.5% or more, and the desk lamp was set so that the polarizing plate became horizontal. The lens subjected to the curving process was placed thereon in a manner such that the convex surface of the lens contacted with the polarizing plate. In that state, the lens was rotated, and visual observation of iridescent patterns was carried out at a position where interference stripes due to optical distortion were seen most clearly.

(Preparation of Special Polycarbonate Sheet A2)

13.22 kg (30.10 mol) of 9,9-bis(4-(2-hydroxyethoxyl) phenyl)fluorene, 6.14 kg (28.7 mol) of diphenyl carbonate and 0.0152 g ($1.81 \times 10^{-4}$ mol) of sodium hydrogen carbonate were put into a 50 L reactor equipped with a stirring machine and a distillation apparatus, and the mixture was heated to 215° C. under nitrogen atmosphere of 760 Torr over 1 hour and stirred. After that, the degree of pressure reduction was adjusted to 150 Torr over 15 minutes, and the mixture was held at 215° C. under 150 Torr for 20 minutes and a transesterification reaction was performed. Further, the temperature was increased to 240° C. at a rate of 37.5° C./hr, and the mixture was held at 240° C. under 150 Torr for 10 minutes. After that, the degree of pressure reduction was adjusted to 120 Torr over 10 minutes, and the mixture was held at 240° C. under 120 Torr for 70 minutes. After that, the degree of pressure reduction was adjusted to 100 Torr over 10 minutes, and the mixture was held at 240° C. under 100 Torr for 10 minutes. Further, the degree of pressure reduction was adjusted to 1 Torr or less over 40 minutes, and a polymerization reaction was performed with stirring at 240°

C. under 1 Torr or less for 10 minutes. After the reaction was completed, nitrogen was blown into the reactor for pressurization, and a polycarbonate resin produced was taken out while being pelletized. 7 kg of the obtained pellet of the polycarbonate resin (9,9-bis(4-(2-hydroxyethoxyl)phenyl) fluorene: 15.94 mol) and 0.59 kg of a pellet of a polycarbonate resin consisting of bisphenol A (trade name: Iupilon E-2000, Mitsubishi Engineering-Plastics Corporation) (bisphenol A: 2.32 mol) were shaken up well, and the mixture was kneaded and pelletized at 260° C. using an extruder, thereby obtaining 5.4 kg of a blend pellet. Tg of the obtained blend pellet was 148° C.

The blend pellet was vacuum-dried at 100° C. for 24 hours, and then a film was formed at a cylinder temperature of 250° C., a die temperature of 250° C. and a roll temperature of 135° C., thereby obtaining a special polycarbonate sheet A2 having a thickness of 300 μm. Regarding the obtained special polycarbonate sheet A2, the photoelastic coefficient was $37 \times 10^{-12}$ m$^2$/N, the retardation value (Re) at a wavelength of 600 nm was 3.2 nm, and the moisture vapor transmission rate was 19 g/m$^2$/day.

(Preparation of Polycarbonate Sheet B)

21.95 kg (50.0 mol) of 9,9-bis(4-(2-hydroxyethoxyl)phenyl)fluorene, 9.80 kg (50.0 mol) of tricyclo[5.2.1.0$^{2,6}$]decanedimethanol, 21.85 kg (52.0 mol) of diphenyl carbonate and $2.5 \times 10^{-3}$ g ($3 \times 10^{-5}$ mol) of sodium hydrogen carbonate were put into a 50 L reactor equipped with a stirring machine and a distillation apparatus, and the mixture was heated to 215° C. under nitrogen atmosphere of 760 Torr over 1 hour and stirred.

After that, the degree of pressure reduction was adjusted to 150 Torr over 15 minutes, and the mixture was held at 215° C. under 150 Torr for 20 minutes and a transesterification reaction was performed. Further, the temperature was increased to 240° C. at a rate of 37.5° C./hr, and the mixture was held at 240° C. under 150 Torr for 10 minutes. After that, the degree of pressure reduction was adjusted to 120 Torr over 10 minutes, and the mixture was held at 240° C. under 120 Torr for 70 minutes. After that, the degree of pressure reduction was adjusted to 100 Torr over 10 minutes, and the mixture was held at 240° C. under 100 Torr for 10 minutes. Further, the degree of pressure reduction was adjusted to 1 Torr or less over 40 minutes, and a polymerization reaction was performed with stirring at 240° C. under 1 Torr or less for 10 minutes. After the reaction was completed, nitrogen was blown into the reactor for pressurization, and a polycarbonate resin produced was taken out while being pelletized. Regarding the obtained polycarbonate resin, the molecular weight (Mw) was 64500 and the glass-transition temperature (Tg) was 125° C. 10.0 kg of this polycarbonate resin was vacuum-dried at 100° C. for 24 hours, and to the resin, 1000 ppm of a high-molecular-weight antioxidant (trade name: IRGANOX1010, BASF Japan Ltd.) was added and 500 ppm of a phosphorus-based antioxidant (ADK STAB PEP-36, ADEKA Co., Ltd.) was added, and the mixture was kneaded and pelletized at 250° C. using an extruder, thereby obtaining a pellet. The molecular weight (Mw) of the pellet was 63500. The pellet was vacuum-dried at 100° C. for 24 hours, and then a film was formed at a cylinder temperature of 250° C., a die temperature of 250° C. and a roll temperature of 135° C., thereby obtaining a polycarbonate sheet B having a thickness of 300 μm. Regarding the obtained polycarbonate sheet B, the photoelastic coefficient was $27 \times 10^{-12}$ m$^2$/N, the retardation value at a wavelength of 600 nm was 4.8 nm, and the moisture vapor transmission rate was 15 g/m$^2$/day.

(Preparation of Polarizing Film A)

Polyvinyl alcohol (Kuraray Co., Ltd., trade name: Kuraray vinylon #750) was stained in an aqueous solution containing 0.25 g/L of Chlorantine Fast Red (C.I. 28160), 0.18 g/L of Chrysophenine (C.I. 24895), 1.0 g/L of Solophenyl Blue 4GL (C.I. 34200) and 10 g/L of sodium sulfate at 35° C. for 3 minutes, and then stretched 4-fold in the solution. Next, this stained sheet was immersed in an aqueous solution containing 2.5 g/L of nickel acetate and 6.6 g/L of boric acid at 35° C. for 3 minutes. After that, the sheet was dried at room temperature for 3 minutes in a state where the tension was retained, and then subjected to a heating treatment at 70° C. for 3 minutes, thereby obtaining a polarizing film A.

(Polycarbonate for Injection Molding)

As a polycarbonate for injection molding, a bisphenol A-type aromatic polycarbonate resin (Mitsubishi Engineering-Plastics Corporation, CLS3400) was used.

Example 1

Using a urethane resin-based adhesive, the special polycarbonate sheet A1 (Tg=145° C.) was bonded to one surface of the polarizing film A, and a bisphenol A-type aromatic polycarbonate sheet having a thickness of 0.3 mm (Mitsubishi Gas Chemical Company, Inc., retardation value: 300 nm, Tg=145° C.) was bonded to the other surface of the film, thereby preparing a multilayer polarizing sheet.

Figure 1:
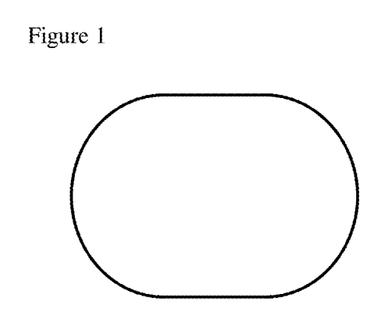
FIG. 1 shows an example of the shape of a polarizing sheet made by punching.
Figure 2:
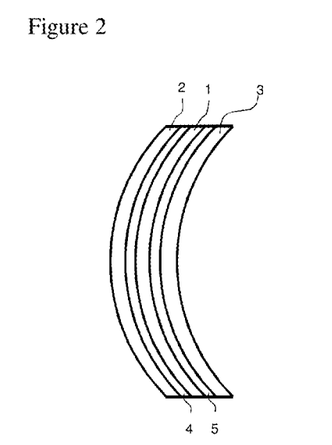
FIG. 2 is a schematic configuration diagram showing an example of the multilayer polarizing lens of the present invention.
Figure 5:
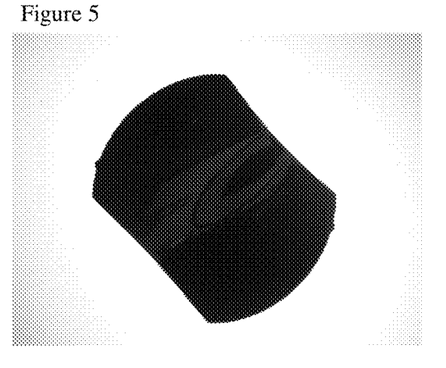
FIG. 5 shows the result of observation of iridescent patterns of Example 1.

This multilayer polarizing sheet was punched into a strip shape by a die, whose basic shape is a true circle having a diameter of 79.5 mm, and by which the width in the vertical direction is cut to 55 mm, as shown in FIG. 1, and the curving process was carried out using a mold having a base curve of 7.95 (curvature radius 66.67 mm), thereby preparing a multilayer polarizing lens as shown in FIG. 2. In the curving process, forming was carried out under the following conditions: mold temperature: 138° C., and retention time: 120 seconds. The base curve as used herein refers to a curvature of the front surface of the lens, and it is a value obtained by dividing 530 by the curvature radius (unit of millimeter). Regarding the multilayer polarizing lens, observation of iridescent patterns and measurement of the resolution were carried out. As a result, no iridescent pattern was observed as shown in FIG. 5, and the resolution was 12. Subsequently, the lens was subjected to shape processing and attached to a frame, thereby preparing a special polycarbonate polarizing eyewear.

Example 2

Figure 3:
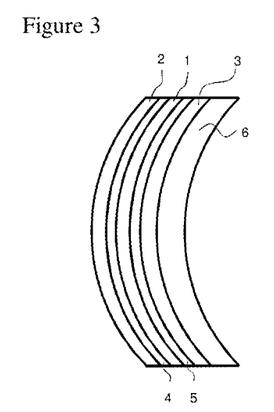
FIG. 3 is a schematic configuration diagram showing an example of the multilayer polarizing lens of the present invention.

The multilayer polarizing lens prepared in Example 1 was inserted in a mold for injection molding, and a melted polycarbonate was injection-molded on the concave surface side of the lens, thereby preparing a multilayer polarizing lens as shown in FIG. 3. At the time of injection molding, a mold having a base curve of 7.932 (curvature radius 66.81 mm), by which 2 multilayer polarizing lenses can be simultaneously formed at one injection, was used, and forming was carried out under the following conditions: measurement value: 40 mm, cylinder temperature: 300° C., mold temperature: 120° C., injection velocity: 25 mm/sec, pressure keeping: 60 MPa, and V-P switching position: 8 mm Regarding the multilayer polarizing lens, observation of iridescent patterns and measurement of the resolution were carried out. As a result, no iridescent pattern was observed, and the resolution was 17. Subsequently, the lens was subjected to shape processing and attached to a frame, thereby preparing a special polycarbonate polarizing eyewear.

Example 3

A multilayer polarizing lens was prepared in a manner similar to that in Example 1, except that the special polycarbonate sheet A1 was changed to the special polycarbonate sheet A2. Regarding the multilayer polarizing lens, observation of iridescent patterns and measurement of the resolution were carried out. As a result, no iridescent pattern was observed, and the resolution was 12. Subsequently, the lens was subjected to shape processing and attached to a frame, thereby preparing a special polycarbonate polarizing eyewear.

Example 4

The multilayer polarizing lens prepared in Example 3 was inserted in a mold for injection molding, and a melted polycarbonate was injection-molded on the concave surface side of the lens, thereby preparing a multilayer polarizing lens as shown in FIG. 3. At the time of injection molding, a mold having a base curve of 7.932 (curvature radius 66.81 mm), by which 2 multilayer polarizing lenses can be simultaneously formed at one injection, was used, and forming was carried out under the following conditions: measurement value: 40 mm, cylinder temperature: 300° C., mold temperature: 120° C., injection velocity: 25 mm/sec, pressure keeping: 60 MPa, and V-P switching position: 8 mm Regarding the multilayer polarizing lens, observation of iridescent patterns and measurement of the resolution were carried out. As a result, no iridescent pattern was observed, and the resolution was 17. Subsequently, the lens was subjected to shape processing and attached to a frame, thereby preparing a special polycarbonate polarizing eyewear.

Comparative Example 1

A multilayer polarizing lens was prepared in a manner similar to that in Example 1, except that the special polycarbonate sheet A1 (Tg=145° C.) was changed to the polycarbonate sheet B (Tg=125° C.). Regarding the multilayer polarizing lens, observation of iridescent patterns and measurement of the resolution were carried out. As a result, no iridescent pattern was observed, and the resolution was less than 12. Subsequently, the lens was subjected to shape processing and attached to a frame, thereby preparing a polycarbonate polarizing eyewear.

Comparative Example 2

The multilayer polarizing lens prepared in Comparative Example 1 was inserted in a mold for injection molding, and a melted polycarbonate was injection-molded on the concave surface side of the lens, thereby preparing a multilayer polarizing lens as shown in FIG. 3. At the time of injection molding, a mold having a base curve of 7.932 (curvature radius 66.81 mm), by which 2 multilayer polarizing lenses can be simultaneously formed at one injection, was used, and forming was carried out under the following conditions: measurement value: 40 mm, cylinder temperature: 300° C., mold temperature: 120° C., injection velocity: 25 mm/sec, pressure keeping: 60 MPa, and V-P switching position: 8 mm Regarding the multilayer polarizing lens, observation of iridescent patterns and measurement of the resolution were carried out. As a result, no iridescent pattern was observed, and the resolution was less than 12. Subsequently, the lens was subjected to shape processing and attached to a frame, thereby preparing a polycarbonate polarizing eyewear.

Comparative Example 3

To both the surfaces of the polarizing film A, a bisphenol A-type aromatic polycarbonate sheet having a thickness of 0.3 mm and a retardation value of 5500 nm (Mitsubishi Gas Chemical Company, Inc., Tg=145° C.) was bonded with a urethane resin-based adhesive so that both the stretch axis of the aromatic polycarbonate sheet and the stretch axis of the polarizing film A were in the horizontal direction of the multilayer polarizing lens, thereby preparing an aromatic polycarbonate polarizing sheet.

This aromatic polycarbonate polarizing sheet was punched into a strip shape by a die, whose basic shape is a true circle having a diameter of 79.5 mm, and by which the width in the vertical direction is cut to 55 mm, as shown in FIG. 1, and the curving process was carried out using a mold having a base curve of 7.95 (curvature radius 66.67 mm), thereby preparing a multilayer polarizing lens as shown in FIG. 2. In the curving process, forming was carried out under the following conditions: mold temperature: 138° C., and retention time: 120 seconds. Regarding the multilayer polarizing lens, observation of iridescent patterns and measurement of the resolution were carried out. As a result, no iridescent pattern was observed, and the resolution was less than 12. Subsequently, the lens was subjected to shape processing and attached to a frame, thereby preparing a polarizing eyewear.

Comparative Example 4

The multilayer polarizing lens prepared in Comparative Example 3 was inserted in a mold for injection molding, and a melted polycarbonate was injection-molded on the concave surface side of the lens, thereby preparing a multilayer polarizing lens as shown in FIG. 3. At the time of injection molding, a mold having a base curve of 7.932 (curvature radius 66.81 mm), by which 2 multilayer polarizing lenses can be simultaneously formed at one injection, was used, and forming was carried out under the following conditions: measurement value: 40 mm, cylinder temperature: 300° C., mold temperature: 120° C., injection velocity: 25 mm/sec, pressure keeping: 60 MPa, and V-P switching position: 8 mm Regarding the multilayer polarizing lens, observation of iridescent patterns and measurement of the resolution were carried out. As a result, no iridescent pattern was observed, and the resolution was less than 12. Subsequently, the lens was subjected to shape processing and attached to a frame, thereby preparing a polarizing eyewear.

Comparative Example 5

To both the surfaces of the polarizing film A, a polycarbonate sheet having a thickness of 0.3 mm (Mitsubishi Gas Chemical Company, Inc., retardation value: 300 nm) was bonded with a urethane resin-based adhesive, thereby preparing an aromatic polycarbonate polarizing sheet.

Figure 6:
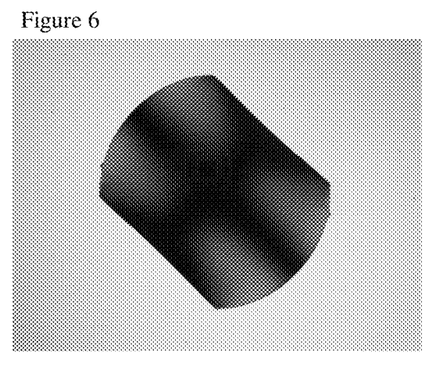
FIG. 6 shows the result of observation of iridescent patterns of Comparative Example 5.
Figure 7:
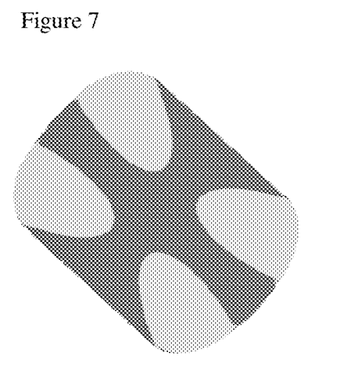
FIG. 7 is a pattern diagram showing the result of observation of iridescent patterns of Comparative Example 5.

This aromatic polycarbonate polarizing sheet was punched into a strip shape by a die, whose basic shape is a true circle having a diameter of 79.5 mm, and by which the width in the vertical direction is cut to 55 mm, as shown in FIG. 1, and the curving process was carried out using a mold having a base curve of 7.95 (curvature radius 66.67 mm), thereby preparing a polarizing lens as shown in FIG. 2. In the curving process, forming was carried out under the following conditions: mold temperature: 138° C., and retention time: 120 seconds. Regarding the multilayer polarizing lens, observation of iridescent patterns and measurement of the resolution were carried out. As a result, iridescent patterns were observed as shown in FIG. 6, and the resolution was 12. Subsequently, the lens was subjected to shape processing and attached to a frame, thereby preparing a polarizing eyewear.

Comparative Example 6

The multilayer polarizing lens prepared in Comparative Example 5 was inserted in a mold for injection molding, and a melted polycarbonate was injection-molded on the concave surface side of the lens, thereby preparing a multilayer polarizing lens as shown in FIG. 3. At the time of injection molding, a mold having a base curve of 7.932 (curvature radius 66.81 mm), by which 2 multilayer polarizing lenses can be simultaneously formed at one injection, was used, and forming was carried out under the following conditions: measurement value: 40 mm, cylinder temperature: 300° C., mold temperature: 120° C., injection velocity: 25 mm/sec, pressure keeping: 60 MPa, and V-P switching position: 8 mm Regarding the multilayer polarizing lens, observation of iridescent patterns and measurement of the resolution were carried out. As a result, iridescent patterns were observed, and the resolution was 17. Subsequently, the lens was subjected to shape processing and attached to a frame, thereby preparing a polarizing eyewear.

Comparative Example 7

To both the surfaces of the polarizing film A, the special polycarbonate sheet A1 (Tg=145° C.) was bonded with a urethane resin-based adhesive, thereby preparing a multilayer polarizing sheet.

This multilayer polarizing sheet was punched into a strip shape by a die, whose basic shape is a true circle having a diameter of 79.5 mm, and by which the width in the vertical direction is cut to 55 mm, as shown in FIG. 1, and the curving process was carried out using a mold having a base curve of 7.95 (curvature radius 66.67 mm) In the curving process, forming was carried out under the following conditions: mold temperature: 138° C., and retention time: 120 seconds. Subsequently, it was inserted in a mold for injection molding, and a melted polycarbonate was injection-molded on the concave surface side of the lens, thereby preparing a multilayer polarizing lens. At the time of injection molding, a mold having a base curve of 7.932 (curvature radius 66.81 mm), by which 2 multilayer polarizing lenses can be simultaneously formed at one injection, was used, and forming was carried out under the following conditions: measurement value: 40 mm, cylinder temperature: 300° C., mold temperature: 120° C., injection velocity: 25 mm/sec, pressure keeping: 60 MPa, and V-P switching position: 8 mm Regarding the multilayer polarizing lens, observation of iridescent patterns and measurement of the resolution were carried out. As a result, no iridescent pattern was observed, and the resolution was 17. However, flow patterns derived from the special polycarbonate resin melted at the time of injection molding were observed, and the lens had poor outer appearance. Subsequently, the lens was subjected to shape processing and attached to a frame, thereby preparing a polycarbonate polarizing eyewear.

The results regarding the observation of iridescent patterns, resolution and presence or absence of injection molding of the eyewear prepared in Examples 1-4 and Comparative Examples 1-7 are shown below. In this regard, Tg is a glass-transition temperature and Re is a retardation value.

TABLE 1

|  | Sheet on convex surface side | Sheet on concave surface side | Results of observation of iridescent patterns | Resolution | Injection molding |
|---|---|---|---|---|---|
| Example 1 | Special polycarbonate sheet A1 (Content of specific compound*[1]: 87 mol %, Tg = 145° C., Re = 3.6 nm) | Aromatic polycarbonate sheet (Tg = 145° C., Re = 300 nm) | No iridescent pattern | 12 | absent |
| Example 2 | Special polycarbonate sheet A1 (Content of specific compound: 87 mol %, Tg = 145° C., Re = 3.6 nm) | Aromatic polycarbonate sheet (Tg = 145° C., Re = 300 nm) | No iridescent pattern | 17 | present |
| Example 3 | Special polycarbonate sheet A2 (Content of specific compound: 87 mol %, Tg = 148° C., Re = 3.2 nm) | Aromatic polycarbonate sheet (Tg = 145° C., Re = 300 nm) | No iridescent pattern | 12 | absent |

TABLE 1-continued

| | Sheet on convex surface side | Sheet on concave surface side | Results of observation of iridescent patterns | Resolution | Injection molding |
|---|---|---|---|---|---|
| Example 4 | Special polycarbonate sheet A2 (Content of specific compound: 87 mol %, Tg = 148° C., Re = 3.2 nm) | Aromatic polycarbonate sheet (Tg = 145° C., Re = 300 nm) | No iridescent pattern | 17 | present |
| Comparative Example 1 | Polycarbonate sheet B (Content of specific compound: 50 mol %, Tg = 125° C., Re = 4.8 nm) | Aromatic polycarbonate sheet (Tg = 145° C., Re = 300 nm) | No iridescent pattern | less than 12 | absent |
| Comparative Example 2 | Polycarbonate sheet B (Content of specific compound: 50 mol %, Tg = 125° C., Re = 4.8 nm) | Aromatic polycarbonate sheet (Tg = 145° C., Re = 300 nm) | No iridescent pattern | less than 12 | present |
| Comparative Example 3 | Aromatic polycarbonate sheet (Tg = 145° C., Re = 5500 nm) | Aromatic polycarbonate sheet (Tg = 145° C., Re = 5500 nm) | No iridescent pattern | less than 12 | absent |
| Comparative Example 4 | Aromatic polycarbonate sheet (Tg = 145° C., Re = 5500 nm) | Aromatic polycarbonate sheet (Tg = 145° C., Re = 5500 nm) | No iridescent pattern | less than 12 | present |
| Comparative Example 5 | Aromatic polycarbonate sheet (Tg = 145° C., Re = 300 nm) | Aromatic polycarbonate sheet (Tg = 145° C., Re = 300 nm) | Iridescent patterns were observed | 12 | absent |
| Comparative Example 6 | Aromatic polycarbonate sheet (Tg = 145° C., Re = 300 nm) | Aromatic polycarbonate sheet (Tg = 145° C., Re = 300 nm) | Iridescent patterns were observed | 17 | present |
| Comparative Example 7*[2] | Special polycarbonate sheet A1 (Tg = 145° C., Re = 3.6 nm) | Special polycarbonate sheet A1 (Tg = 145° C., Re = 3.6 nm) | No iridescent pattern | 17 | present |

*[1]Content of specific compound: the content of the compound represented by general formula (1) in the whole dihydroxy compound constituting the resin included in the sheet.

*[2]Comparative Example 7: Poor outer appearance (flow patterns were observed).

EXPLANATIONS OF LETTERS OR NUMERALS

1 polarizing film
2 special polycarbonate sheet
3 aromatic polycarbonate sheet
4, 5 adhesive layer
6 aromatic polycarbonate

The invention claimed is:

1. An eyewear which uses a polarizing lens obtained by bending a multilayer polarizing sheet in which a sheet (A) including at least 50% by mass of an aromatic polycarbonate resin and having a retardation value of 2000 nm or less at a wavelength of 600 nm is layered on one side of a polarizing film, and a sheet (B) including a special polycarbonate resin obtained by carbonate bonding a dihydroxy compound through use of a carbonic acid diester, the polycarbonate resin being a compound in which 70 to 100 mol % of the dihydroxy compound is represented by general formula (1), is layered on the other side of the polarizing film:

general formula (1)

wherein in general formula (1), $R_1$ and $R_2$ are each independently a hydrogen atom, a $C_1$-$C_{20}$ alkyl group, a $C_1$-$C_{20}$ alkoxyl group, a $C_5$-$C_{20}$ cycloalkyl group, a $C_5$-$C_{20}$ cycloalkoxyl group, a $C_6$-$C_{20}$ aryl group or a $C_6$-$C_{20}$ aryloxy group; and Xs are each independently a $C_2$-$C_8$ alkylene group, a $C_5$-$C_{12}$ cycloalkylene group or a $C_6$-$C_{20}$ arylene group.

2. The eyewear according to claim 1, wherein 80 to 95 mol % of the whole dihydroxy compound constituting the resin included in the sheet (B) is a compound represented by general formula (1).

3. The eyewear according to claim 1, wherein the resin included in the sheet (B) consists of only the special polycarbonate resin; 80 to 95 mol % of the dihydroxy compound constituting the special polycarbonate resin is a compound represented by general formula (1); and the remaining 20 to 5 mol % of the dihydroxy compound is a dihydroxy compound other than the compound represented by general formula (1).

4. The eyewear according to claim 1, wherein the resin included in the sheet (B) consists of the special polycarbonate resin and an aromatic polycarbonate resin; 100 mol % of the dihydroxy compound constituting the special polycarbonate resin is a compound represented by general formula (1); the dihydroxy compound constituting the aromatic polycarbonate resin is a dihydroxy compound other than the compound represented by general formula (1); and 80 to 95 mol % of the whole dihydroxy compound constituting the resin included in the sheet (B) is the compound represented by general formula (1).

5. The eyewear according to claim 1, wherein the temperature difference between the glass-transition temperature of the sheet (B) and the glass-transition temperature of the sheet (A) having a retardation value of 2000 nm or less is 10° C. or less.

6. The eyewear according to claim 1, wherein in the compound represented by general formula (1), $R_1$ and $R_2$ are a hydrogen atom and Xs are an ethylene group.

7. The eyewear according to claim 3, wherein the dihydroxy compound other than the compound represented by general formula (1) is a compound represented by the below-described structural formula (1).

structural formula (1)

8. The eyewear according to claim 3, wherein the dihydroxy compound other than the compound represented by general formula (1) is a compound represented by the below-described general formula (2):

general formula (2)

wherein in general formula (2), Y is a $C_1$-$C_{10}$ alkylene group or a $C_4$-$C_{20}$ cycloalkylene group.

9. The eyewear according to claim 8, wherein the compound represented by general formula (2) is at least one selected from tricyclo[5.2.1.0$^{2,6}$]decanedimethanol, cyclohexane-1,4-dimethanol and pentacyclopentadecanedimethanol.

10. The eyewear according to claim 8, wherein the compound represented by general formula (2) is tricyclo[5.2.1.0$^{2,6}$]decanedimethanol.

11. The eyewear according to claim 1, wherein the retardation value of the sheet (B) at a wavelength of 600 nm is 20 nm or less.

12. The eyewear according to claim 1, which is subjected to a curving process to have a spherical or non-spherical surface so that the surface at the sheet (B) side becomes a convex surface.

13. The eyewear according to claim 12, wherein an aromatic polycarbonate resin is further injection-molded on the concave surface.

* * * * *